US000001985H

(19) United States

(12) Statutory Invention Registration (10) Reg. No.: US H1985 H

Ligler et al. (43) Published: Aug. 7, 2001

(54) METHOD FOR DETECTING BIOLOGICAL TOXINS

(75) Inventors: Frances S. Ligler, Potomac; James R. Campbell, Olney, both of MD (US)

(73) Assignee: The United States of America as represented by the Secretary of the Navy, Washington, DC (US)

(21) Appl. No.: 07/818,600

(22) Filed: Jan. 9, 1992

(51) Int. Cl.[7] ..... C12Q 1/68; C12P 19/34; C12N 9/00

(52) U.S. Cl. ..... 435/6; 435/91.2; 435/183; 536/23.1; 536/24.33

(58) Field of Search ..... 435/6, 91, 91.2; 935/77, 78

(56) References Cited

U.S. PATENT DOCUMENTS

| | | | | |
|---|---|---|---|---|
| 4,221,866 | | 9/1980 | Cotter | 435/4 |
| 4,666,837 | | 5/1987 | Harford et al. | 435/68 |
| 4,675,283 | | 6/1987 | Roninson | 435/6 |
| 4,683,195 | | 7/1987 | Mullis et al. | 435/6 |
| 4,683,202 | | 7/1987 | Mullis | 435/91 |
| 4,689,401 | | 8/1987 | Ferris | 530/396 |
| 4,921,794 | | 5/1990 | Tabor et al. | 435/91 |
| 4,925,792 | | 5/1990 | Rappuoli | 435/69.1 |
| 4,962,020 | | 10/1990 | Tabor et al. | 435/6 |
| 4,965,188 | * | 10/1990 | Mullis et al. | 435/6 |
| 4,994,368 | | 2/1991 | Goodman et al. | 435/6 |
| 4,994,370 | | 2/1991 | Silver et al. | 435/6 |
| 4,994,372 | | 2/1991 | Tabor et al. | 435/6 |
| 5,001,050 | | 3/1991 | Blanco et al. | 435/5 |
| 5,008,182 | | 4/1991 | Sninsky et al. | 435/5 |
| 5,021,335 | | 6/1991 | Tecott et al. | 435/6 |
| 5,035,996 | * | 7/1991 | Hartley | 435/6 |
| 5,536,648 | * | 7/1996 | Kemp et al. | 435/91.2 |

FOREIGN PATENT DOCUMENTS

| | | |
|---|---|---|
| 2-219599 | 9/1990 | (JP) . |
| 90/06376 | 6/1990 | (WO) . |
| 90/11374 | 10/1990 | (WO) . |
| 91/00363 | 1/1991 | (WO) . |
| 91/02817 | 3/1991 | (WO) . |

OTHER PUBLICATIONS

Olive, D. M. Detection of Enterotoxigenic *Escherichia coli* after Polymerase Chain Reaction Amplification . . . J. Clin. Microbiol. (Feb. 1989) 27:261–265.*

Locus CBBOTAG from EMBL data library (Created May 7, 1990).*

* cited by examiner

*Primary Examiner*—Michael J. Carone

*Assistant Examiner*—Aileen J. Baker

(74) *Attorney, Agent, or Firm*—Barry A. Edelberg; Amy Loch Ressing

(57) ABSTRACT

Biological toxins are indirectly detected by using polymerase chain reaction to amplify unique nucleic acid sequences coding for the toxins or enzymes unique to toxin synthesis. Buffer, primers coding for the unique nucleic acid sequences and an amplifying enzyme are added to a sample suspected of containing the toxin. The mixture is then cycled thermally to exponentially amplify any of these unique nucleic acid sequences present in the sample. The amplified sequences can be detected by various means, including fluorescence. Detection of the amplified sequences is indicative of the presence of toxin in the original sample. By using more than one set of labeled primers, the method can be used to simultaneously detect several toxins in a sample.

25 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR DETECTING BIOLOGICAL TOXINS

BACKGROUND OF THE INVENTION

1. Field of the Invention

This invention relates to detecting biological toxins and, more particularly, to a method for amplifying genes coding for the toxins and detecting the amplified genes, which detection is indicative of the presence of the toxins.

2. Description of the Related Art

The ability to detect the presence or absence of biological toxins, such as botulin (a toxin produced by the bacteria *Clostrium botulinum*) or aflatoxins (a toxin produced by the fungus *Aspergillus favus*) contaminating food, various biological warfare agents contaminating the air, and various contaminants of water or biological samples, has been a desire of scientists for ages. Such an ability would help prevent disease, incapacitation or other maladies attributable to the toxins, and would be useful in countering the use of biological weapons.

Current tests for detecting toxins usually depend on chromatographic techniques, such as gas or high-pressure-liquid chromatography, mass spectroscopy, in vivo tests or in vitro bioassays. In vivo tests involve injecting the toxin into animals, usually mice, at varying doses to determine lethality. In vitro bioassays rely on the use of an antibody, receptor or living cell that binds the toxin directly. Thus, the actual toxin is sought to be detected.

In other cases, assay methods are used to detect an organism which is the source of the toxin. For example, if a pathogenic organism is known to be associated directly with a toxin, tests have sought to detect the presence of the pathogen. Such tests may include culturing the live organism.

The conventional tests described above generally are not very sensitive. They also may require pre-concentration of a sample suspected of containing the toxin or organism. Further, in some cases, at least partial purification is necessary to remove interfering substances. These steps can be time-consuming and costly.

To date, there has not been developed a quick and efficient method for detecting the presence of a biological toxin in a sample, said detection being possible even if the toxin has been denatured or the organism responsible for producing the toxin is no longer present.

SUMMARY OF THE INVENTION

Accordingly, it is a purpose of the present invention to provide a more sensitive method for detecting biological toxins.

It is another purpose of the present invention to detect toxins in the food service, food preparation and dairy industries.

It is another purpose of the present invention to detect toxins used as offensive biological weapons.

It is another purpose of the present invention to detect genes that have been willfully engineered into otherwise innocuous microorganisms ("weaponized organisms").

It is another purpose of the present invention to provide a method for detecting a biological toxin by testing for the presence of the unique nucleic acid sequence responsible for the synthesis of the toxin or a specific protein (enzyme) used to produce the toxin.

It is another purpose of the present invention to detect a plurality of different biological toxins in the same sample, simultaneously.

It is another purpose of the present invention to detect target nucleic acid sequences using a simple and easy to use method, which detection is indicative of the presence of toxins coded by the sequences.

It is another purpose of the present invention to solve the problems associated with conventional detection of low amounts of biological toxins, of the biological entity responsible for producing the toxin, such as a microorganism, or of the nucleic acids coding for these toxins.

It is another purpose of the present invention to detect the presence in environmental and biological samples, of specific genes that encode toxins, regardless of whether the gene is present in its normal genetic host, or whether it has been inserted into a different host by genetic engineering or by a random, natural gene transfer event.

It is another purpose of the present invention to provide a method for identifying toxins in environmental or biological samples by detecting minute traces of genetic material that encode said toxins, and which are found in association with said toxin preparations as a byproduct of the toxin manufacturing process, such as toxins produced for dissemination as offensive biological weapons.

To achieve the foregoing and other purposes of the present invention there is provided the following method for detecting biological toxins in samples. Instead of trying to directly detect the toxin present, the nucleic acid coding for the toxin is amplified using the known method polymerase chain reaction ("PCR"), and the amplified nucleic acid is then detected as an indication of the presence or absence of the toxin.

More particularly, samples, such as clinical, food, water supply or air samples, suspected of containing biological toxins are collected. With the unique gene sequence coding for the toxin being known, a primer pair can be selected which is complementary to the gene sequence. The primers and an appropriate enzyme for amplification are then mixed with the sample. The preparation is then placed into a thermal cycler, wherein PCR amplifies any toxin gene present. Thereafter, methods are used to detect the amplified gene. Detection of the gene coding for a toxin is indicative of the presence of the toxin in the original sample.

DESCRIPTION OF THE PREFERRED EMBODIMENTS

It is known that large quantities of proteins and small molecules can be produced by fermentation. For pharmaceutical applications, the products are carefully purified and screened to remove residual DNA. On the other hand, if the products are to be used for environmental applications, such as bioremediation or biological warfare, large quantities are made but rigorous purification is not performed, because costs are too high and there is no need for purification. The DNA coding for the product or for proteins (enzymes) that make the product remains with the product as a contaminant. The DNA is usually at too low a concentration to be detected by conventional methods.

Methods are known for multiplying the DNA, such as the recombinant and cloning techniques discussed in U.S. Pat. Nos. 4,675,283, Roninson; 4,925,792, Rappuoli; or 4,666,837 and Harford et al. However, such methods are not very fast, and the amount of the DNA produced still may not be enough to ensure accurate detection of the genetic material.

Another available method of amplification is known as polymerase chain reaction ("PCR"). With PCR nucleic acid sequences can be quickly and exponentially amplified for facilitated detection of the sequences.

More particularly, as described in U.S. Pat. Nos. 4,683,202, Mullin; 4,683,195, Mullis et al.; and 5,008,182, Sninsky et al.; as well as Saiki et al., Science, 230, 1350–1354 (1985); and Saiki et al., Science, 239, 487–491 (1988), the disclosures of which are expressly incorporated herein, PCR allows in vitro amplification of a nucleic acid sequence which lies between two regions of a known, longer sequence.

More particularly, double-stranded target nucleic acid is first melted to separate the nucleic acid into the two strands to form templates, and then oligonucleotide ("oligo") primers complementary to the ends of the segment which is desired to be amplified are separately annealed to the templates. The oligos serve as primers for the synthesis of new complementary strands, using a polymerase enzyme and a process known as primer extension. The orientation of the primers with respect to one another is such that a 5' to 3' extension product from each primer contains, when extended far enough, the sequence which is complementary to the other oligo. Thus, each newly synthesized nucleic acid strand becomes a template for synthesis of another nucleic acid strand beginning with the other oligo as a primer. Repeated cycles of melting, annealing of oligo primers, and primer extension lead to doubling, with each cycle, of the strands containing the sequence of the template beginning with the sequence of one oligo and extending with the sequence of the other oligo. The cycling is therefore exponential and after about 20–30 cycles, the target nucleic acid can be amplified a million fold.

A critical difference between the present invention and existing PCR-based diagnostic assays is that the existing assays all seek to identify the presence in a sample of the actual infectious organism itself. In these cases, it is the virus or bacteria, such as the HIV virus, that is the causative agent sought to be detected. Some existing assays are described in U.S. Pat. No. 5,008,182 and PCT Published Application No. WO 90/06376.

With the present invention, the organism itself is of no concern. Rather, the present invention focuses on a specific product, usually protein based, produced by an organism. This product, a toxin, is encoded by a unique gene. The present invention seeks to identify the presence of that unique gene in a sample, thereby strongly inferring the presence of the product.

The source of the toxin can be animal, plant or microorganism. However, in all cases the target of the assay is a non-toxic contaminant (DNA or RNA) rather than the actual toxin product or the organism itself.

Moreover, as suggested above, existing rapid assays for toxins often employ the strategy of antibody-based detection utilizing proven formats such as ELISA or RIA. These antibody-based systems employ no type of amplification of nucleic acid sequences. Rather, their sensitivity and specificity depend on highly restricted binding between antibody and target antigens (toxins). In this regard, the toxin products of genetically altered toxin genes, while retaining their toxic potential, may not be detectable by antibody assays developed for the unaltered toxin. This is not the case for the assay according to the present invention, in which the gene, even if altered, is detectable using PCR technology, which requires significant, but not 100%, homology between the priming sequences and only the ends or flanking regions of the DNA to be amplified.

Further, any test that concentrates on detecting an organism and not the toxin per se may be rendered useless when the organism is no longer present or no longer viable. For example, it is frequently not an organism per se in food that causes illness, but a toxin produced by the organism. Testing for the organism, if the organism is not present or not viable, may fail to identify the presence of the toxin. In contrast, with this invention, presence of the organism, such as *Clostridium botulinum,* is not needed in order to detect the presence of botulin; only the coincidental presence of the nucleic acid sequence responsible for coding the toxin is needed.

Thus, as described in detail below, the present invention utilizes PCR as a vehicle for quick and efficient amplification of genetic determinants of biological toxins, and then detects the amplified genetic determinants as an indication of the presence or absence of the toxins coded by the genetic material.

According to a preferred method of the present invention, a sample suspected of containing a biological toxin is collected. By "toxin" it is meant a poisonous substance of biological origin, which necessarily excludes synthetic toxins which contain no contaminating DNA. The toxins are usually, but not necessarily, proteins. Nonlimiting examples of protein toxins include botulin, perfringens toxin, mycotoxins, shigatoxins, staphylococcal enterotoxin B, tetanus, ricin, cholera, aflatoxins, diphtheria, T2, seguitoxin, saxitoxin, abrin, cyanoginosin, alphatoxin, tetrodotoxin, aconotoxin, snake venom, scorpion venom and other spider venoms. A nonlimiting example of a non-protein toxin is tricothecene (T-2). Toxin-producing microorganisms of interest include, but are not limited to: *Corynebacterium diphtheriae*, Staphylococci, *Salmonella typhimuium*, Shigellae, *Pseudomonas aeruginosa, Vibrio cholerae, Clostridium botulinum*, and *Clostridium tetani*. A nonlimiting example of a toxin producing plant is *Ricinus communis,* and of a fungus producing a toxin is *Aspergillus favus.*

Gene sequences coding for many toxins, such as botulin toxin types A–E, have been published and are available in a computer data base. If the sequence is not known, the organism responsible for producing the toxin is grown and the DNA removed and analyzed using known methods to determine the appropriate sequence. Since the toxins are very dangerous, e.g. botulin, special precautions must be taken to protect laboratory workers and the general public.

The gene sequence must be specific to a particular organism or else the sequences of several organisms might be amplified using PCR. As a result, once a sequence is detected, it must be checked against related organisms incapable of producing the toxin of interest to ensure that the DNA of the related organism would not be amplified by PCR, or else a nonspecific reading would occur.

With non-protein toxins, one looks for the gene that encodes an enzyme that is very specific for and critical to the production of the toxin.

The sample suspected of containing a toxin can be from any source. For example, an environmental (such as air, water, soil, surface swipes) or biological (blood, mucous, saliva) sample can be used, provided it contains or is suspected of containing the unique nucleic acid sequence, i.e., "target" nucleic acid, responsible for producing the toxin.

The sample is first processed, if necessary (centrifugation, addition of lysing agents), to obtain a crude preparation which contains at least a fraction of any target nucleic acid that may be present in the sample. For example, before amplification the sample may be treated with an amount of a known reagent effective to open cells, etc., in the sample, and to expose the strands of the nucleic acids. These lysing and denaturing steps allow amplification to occur much more readily.

If not already aqueous, an aqueous extract of the sample is prepared.

For the purpose of safety, a protein toxin can be denatured, for example, by the addition of phenol. This treatment does not affect the DNA and the solution is centrifuged to separate the DNA portion.

It is also necessary to separate the strands before the genetic material can be used as a template, either as a separate step or simultaneously with the synthesis of the primer extension products. This strand separation step can be accomplished by using any known suitable denaturing conditions, including physical, chemical or enzymatic means.

The target nucleic acid sequence, i.e. the unique gene responsible for coding for the toxin, which should be contained in the crude preparation, is then amplified by PCR according to the following steps.

The preparation is mixed with an enzyme appropriate for PCR, i.e., an agent for polymerization, a pair of primers, an appropriate buffer(s), and deoxyribonucleotide triphosphates, each of which are described more fully below.

The "agent for polymerization" may be any compound or system, including enzymes, which accomplishes the synthesis of primer extension products. Suitable enzymes for this purpose include, for example, Taq (*Thermus aquaticus*) polymerase, Q-beta replicase, *E. coli* DNA polymerase I, Klenow fragment of *E. coli* DNA polymerase I, T4 DNA polymerase, other available DNA polymerases, reverse transcriptases and other heat-stable enzymes.

The term "primer" as used herein refers to a molecule, comprised of two or more deoxyribonucleotides or ribonucleotides, which is capable of acting as a point for initiating synthesis when placed under conditions which induce the synthesis of a primer extension product substantially complementary to a nucleic acid strand, i.e., in the presence of the deoxyribonucleotide triphosphates and the agent for polymerization and at the suitable temperature and pH. Preferably, the primer is an oligodeoxyribonucleotide.

The primer is preferably single stranded for maximum efficiency in amplification, but may alternatively be double stranded. If double stranded, the primer is first treated to separate its strands before being used to prepare extension products.

The primer's sequence must be complementary to the unique target nucleic acid sequence which is responsible for coding the toxin of interest and appropriate to the goals of the assay, i.e. the primer should be chosen so that the target DNA amplified would be selected with appropriate specificity. In this regard, the primer must be sufficiently long and specific enough to prime the synthesis of the extension products in the presence of the agent for polymerization. Statistically speaking, the primer is preferably at least 12 bases long, to ensure the primer describes a sequence that is unique to that organism. Further, because many organisms share some common conserved sequences, the primer should be specific to the particular type of organism responsible for producing the toxin, and not a closely related but non-toxin producing type.

With the present invention, one can dictate the level of specificity of the assay. One can use primers which will identify toxin producing genes from any of several organisms, by targeting common nucleic acid sequences. For example, if one wanted to detect all *Clostridium botulinum* types in a single sample, e.g. types A–F, theoretically, a primer could be prepared, if the types A–F shared a common nucleic acid sequence responsible for producing the botulin toxin. However, it is not currently known whether such a common nucleic acid sequence exists among *Clostridium botulinum*. A given toxin gene can also be among *Clostridium botulinum* exists. A given toxin gene can also be shared by more than one organism. For example, the heat-labile toxin gene is shared by both *Vibrio cholerae* and toxigenic strains of *Escherichia coli*. Toxin genes transferred into non-native host organisms could also be detected using the method of the present invention. Thus, the primer sequence can be determined and a primer prepared, once the unique sequence of the target nucleic acid is determined. The exact lengths of the primers will depend on many factors, including temperature, buffer, nucleotide composition and source of primer.

PCR occurs in a buffered aqueous solution, preferably at a pH of 7–9, most preferably about 8.

The deoxyribonucleotide triphosphates dATP, dCTP, dGTP and/or TTP are also added to the synthesis mixture, either separately or together with the primers, in adequate amounts and the resulting solution is heated in a thermal cycler according to the following sequence.

1. A high temperature (usually about 94° C.), at which the two strands of the double stranded target melt, or denature, and separate into single strands.
2. A low temperature (37–54° C.), at which the primers bind (anneal) to their homologous regions on the single stranded target.
3. An intermediate temperature (about 72° C.) at which the agent for polymerization, e.g. Taq polymerase, binds to the primer complex and moves down the single stranded target, copying it and making a duplicate second strand.

The exact temperatures for each of the steps must be determined empirically for the particular target to be amplified, although optimum conditions can be estimated, based on certain characteristics of the target.

It is also possible to carry out a two-step temperature cycle wherein the third above-described step is eliminated. This is because in heating from the second step directly back to the first step the reaction passes through the mid-range over a period of time which, although brief, can be sufficient to allow complete primer extension to occur.

This thermal cycle is then repeated until the target DNA has been amplified sufficiently to permit its detection. Typically, the thermal cycle is repeated about 20 to 30 times, resulting in an approximately one million-fold amplification of the target DNA.

A second amplification step can be followed, wherein a second set of primers can introduce a detection label, such as biotin, "double stranded DNA binding protein" (dsDNA-BP) binding sites, or fluorophores into the amplified genes. See Kemp et al., Proc. Natl. Acad. Sci., pp. 2423–2427 (1989) and co-pending, co-assigned U.S. patent application Ser. No. 07/635,019, filed Dec. 28, 1990, in the name of one of the inventors herein, Dr. James Campbell, the subject matter of which is expressly incorporated by reference herein). These labels further facilitate the detection of the amplified nucleic acid sequence, as described below.

According to the teachings of the above-mentioned U.S. Ser. No. 635,019, samples suspected of containing microorganisms or characteristic DNA are processed as appropriate (centrifugation, addition of lysing agents, or no processing) to obtain a crude preparation which contains at least a fraction of any target DNA that may be present in the sample. The sample can be from any source. For example, the sample can be environmental (such as air, water, soil, surface swipes) or biological (blood, urine, feces, etc.).

The target DNA from the crude preparation is then amplified by the polymerase chain reaction. The polymerase chain reaction is a well-known generalized procedure for amplifying target DNA. The polymerase chain reaction is described in Saiki et al, *Science,* 230, 1350–1354 (1985), and Saiki et al, *Science,* 239, 487–491 (1988), both of which are incorporated herein by reference. In general, a sample of the crude preparation is added to an aqueous solution containing an enzyme appropriate for PCR (such as Taq polymerase or Q-beta replicase) appropriate buffers, deoxyribonucleotide triphosphates, and two primers.

The thus prepared reaction mixture is then thermally cycled at three successive temperatures:

1. A high temperature (usually about 94° C.), at which the two strands of the double stranded target DNA melt, or denature, and separate into single strands.
2. A low temperature (37–54° C.), at which the primers bind (anneal) to their homologous regions on the single stranded target DNA.
3. An intermediate temperature (about 72° C.) at which the Taq polymerase binds to the DNA-primer complex and moves down the single stranded target, copying it and making a duplicate second strand. The exact temperatures for each of the steps must be determined empirically for the particular DNA to be amplified, although optimum conditions can be estimated, based on certain characteristics of the DNA. It is also possible to carry out a two-step temperature cycle wherein the third (72° C.) step described herein is eliminated. This is because in heating from the second (37–54° C.) step directly back to the first (94° C.) step the reaction passes through the 72° C. range over a period of time which, although brief, can be sufficient to allow complete primer extension to occur.

This thermal cycle is then repeated until the target DNA has been amplified sufficiently to permit its detection. Typically, the thermal cycle is repeated about 20 to 30 times, resulting in an approximately one million-fold amplification of the target DNA.

The thus amplified target DNA is then subjected to a second, briefer amplification. This second amplification uses a second pair of primers that are nested within the region bracketed by the first set of primers. In other words, the second pair of primers is complementary to, and binds with, sites on the amplified DNA within the region bracketed by the first set of primers.

The second primers also differ from the first primers in that at least one member of the second pair has attached covalently to its 5' end, a fluorescent reporter molecule, (e.g., FITC, TRITC, Rhodamine, Texas Red). In addition, at least one member of the second primer pair has covalently attached to its 5' end a particular DNA fragment that constitutes a specific binding site for a double-stranded DNA binding protein (dsDNA-BP). Typically, the dsDNA-BP is attached to one member of the primer pair and the FRM is attached to the other member of the primer pair. Nevertheless, it is possible to covalently bind both the dsDNA-BP binding site and the FRM to only one of the primers and leave the other primer unmodified. This is accomplished by designing one primer with the dsDNA-BP binding site covalently attached to the 5' end of the primer, and the FRM covalently attached to the 5' end of the binding site. In an evanescent wave detection format, this modification may result in greater sensitivity of the system by bringing the FRM closer to the surface of the optical fiber, for more efficient excitation and more efficient coupling of emitted light back into the fiber. The second amplification is typically shorter than the first amplification and need only be sufficient to ensure that the concentration of twice-amplified DNA, which contains the fluorescent reporter molecule and the double stranded DNA-binding protein, will emit a detectable level of fluorescence energy when the DNA is bound to the sensor and exited by light of an appropriate wavelength.

A dsDNA-BP is attached to a fluorescent sensor by any means appropriate for fixing a protein to the exposed portion of the material of the sensor. Several techniques have been used to attach proteins to various substrates and these techniques may also be useful in the present invention. Typically, the substrate for the dsDNA-BP is made of glass or membrane material and the dsDNA-BP is attached using a technique appropriate for the fixing of a protein to glass or synthetic membranes such as nitrocellulose or PVDF. One technique for immobilizing protein on glass which is particularly useful in the present invention is described by Bhatia et al "Fiber Optic-based Immunosensors: A Progress Report", SPIE vol. 1054 Fluorescence Detection III (1989).

The exposed surface of the sensor having the dsDNA-BP immobilized thereon is then exposed to the twice amplified DNA preparation, which, if it originally contained the target DNA, now contains the amplified target DNA with reporter molecules and dsDNA-BP binding site attached. Any target DNA amplified with the second set of primers will then bind, via the dsDNA binding site, to the dsDNA-BP immobilized on the exposed surface of the sensor. If the sensor is an optical waveguide, the evanescent wave excites the fluorescent reporter molecule, which has been positioned in close proximity to the outer surface of the sensor via binding of the dsDNA-BP with the dsDNA-BP binding site on the DNA. The fluorescence of the excited fluorescent reporter molecule, at a wavelength different from that of the excitation energy, is also readily coupled back into the sensor, which detects the fluorescent emission by known means. If the exposed surface of the sensor is a membrane, the dsDNA-BP is attached to the membrane either by adsorption or by covalent linkage, and unreacted sites on the membrane are blocked by any of several blocking reagents. The twice-amplified DNA is then applied to the membrane, where it binds to the attached protein via the binding site incorporated into the amplified DNA. The membrane is then introduced into a fluorometer, typically via a dipstick or slide device, and fluorescence intensity measured.

Several dsDNA-BP's are known to exist and can be used according to the present invention.

A fluorescent sensor useful according to the present invention can be any one having an exposed surface of a material onto which a dsDNA-BP can be immobilized. Typically, the sensor will have an exposed surface made of a silica-based glass or a plastic, but other materials such as nitrocellulose or PVDF membrane may also be used. The geometry of the waveguide, membrane, or other surface is not critical to the present invention.

Because the primer pair for at least the first amplification step is selected to be homologous to base sequences unique to the target nucleic acid, only the target nucleic acid is amplified. Because the target nucleic acid is greatly amplified, the amplified target becomes essentially the only nucleic acid in the sample preparation after the first amplification step has been completed. Thus, spurious amplification of nucleic acid other than target nucleic acid in any second amplification step is essentially avoided.

Moreover, as individual primers are "invisible" to and do not interact with each other, several different sets of primers can be used simultaneously in the same reaction tube to probe a sample for multiple nucleic acid sequences associated with a number of different biological toxins. By attaching different detection labels to the different primer sets, the presence of different nucleic acids can be determined. This technique provides a unique capability for simultaneous multi-toxin detection, which is not available in conventional detection methods.

A variety of tests can be used to identify the amplified nucleic acid sequences. These tests include dot blots, Southern blots, polyacrylamide or agarose gel electrophoresis, calorimetry, fluorescence, membrane affinity filtration and identification, and differential affinity chromatography, each of which is described below.

In the dot blot method, the amplified sample is spotted directly on a membrane and labeled with a probe. The probe can be an enzyme such as alkaline phosphatase, a radioactive label such as $^{32}P$, a fluorescent label, or biotin. The labelled probe may be detected by spectroscopy, photochemistry or by biochemical, immunochemical or chemical means.

In Southern blots, gel electrophoresis separates DNA fragments into their size classes. The fragments are then denatured by placing the gel in alkali after which a nitrocellulose filter sheet is laid over the gel. The DNA fragments are transferred from the gel to a filter by placing layers of absorbent paper above the latter (blotting), with the gel being immersed in a high concentration of salt. This causes the solute and DNA fragments to diffuse through the nitrocellulose sheet to which the latter are adsorbed, maintaining their relative positions. The nitrocellulose sheet is then incubated under renaturing conditions with a solution containing radiolabelled molecules able to base-pair with some sequence in the original DNA (probing). Finally, the position and therefore fragment size of the complementary sequence in the original DNA can be located by autoradiography or fluorescence. *Chambers Biology Dictionary,* Walker, ed., W. & R. Chambers Ltd. and Cambridge University Press, 1989.

The polyacrylamide or agarose gel method is used for separating nucleic acids or proteins on the basis of charge, shape and size. The highly cross-linked polymer of acrylamide or agarose forms a transparent gel matrix through which macromolecules move under the influence of an electric or magnetic field, resulting in discrete bands of DNA. Id.

The fluorescence method is described in the above-cited co-pending U.S. patent application No. 07/635,019. In this method, the second set of primers is modified so that at least one contains a specific binding site for a dsDNA-BP and at least one has a fluorescent reporter molecule (FRM) covalently attached thereto. The dsDNA-BP is attached to the surface of a fluorometric device by adsorption or covalent interaction. In an assay, the amplification of the target DNA with concomitant inclusion of both the FRM and dsDNA-BP binding site, makes the amplified portion the only DNA detectable by the fluorometric device, such as a fluorescence sensor. The amplified target DNA, with the FRM and the dsDNA-BP binding site attached thereto, specifically binds with the dsDNA-BP on the fluorometric device. This binding brings the FRM close to the surface of the fluorescent fluorometric device, where it can be excited. For fluorometric devices such as evanescent wave-based systems, the close proximity of the FRM to the surface of the fluorometric device enhances both the excitation of the FRM, as well as the coupling of the energy emitted by the excited FRM at a wavelength different than that of the excitation energy) back into the fluorometric device. For fluorometric devices whose exposed binding surface employs a membrane, e.g., in dipstick or slide format, the binding of the fluorescent DNA by the dsDNA-BP permits it to be manipulated in separation steps or for introduction into fluorometric devices. At the photodetector, the signal is discriminated and interpreted by a microprocessor. The entire excitation, emission, detection and interpretation process can occur in seconds.

Membrane affinity filtration and identification involves a membrane attached to an absorptive pad. A "capture reagent", e.g., a dsDNA-BP, is adsorbed to the membrane. The PCR-amplified target DNA, which has on one end a binding site for the dsDNA-BP and on the other end a biotin molecule, is allowed to react 5 minutes in a small test tube with an equal volume of a "color reagent." The color reagent may consist, for example, of streptavidin (a molecule that binds with high affinity to biotin) bound to either colloidal gold, or to a fluorophore. This mixture is then applied to the membrane, where it is rapidly (10 seconds) drawn through by capillary action into the absorptive pad below. The complex is captured via its binding site by the dsDNA-BP. In the case of the colloidal gold label, a positive result is indicated by the immediate appearance of a red spot on the membrane. For the fluorophore label, the membrane is introduced into a fluorometer to measure the fluorescence signal.

Differential affinity chromatography utilizes a membrane or other solid support, such as a commercially available syringe filter unit (i.e., ACTI-DISK®) through which is treated with the PCR product. In the case of the filter, typically a filter disk, is prepared by a two-step procedure: First the dsDNA-BP is covalently bound to the disk. Next, all the binding sites of the dsDNA-BP are occupied by exposure to an extraneous PCR product containing a "low-affinity" binding site for the dsDNA-BP. The "normal" binding site for the dsDNA-BP consists of a specific 10 nucleotide sequence of DNA, whereas the "low-affinity" binding site consists of this 10 nucleotide sequence in which one or more of the nucleotides has been substituted with a different one, to reduce the overall affinity of the product for the dsDNA-BP binding site. This low affinity PCR product also has attached to its other end an enzyme such as horseradish peroxidase or alkaline phosphatase or alternatively, a fluorophore. When the PCR product containing the target DNA with the "normal" binding site is introduced into the filter disk, it easily out-competes the previously bound low-affinity product, which elutes off the membrane and falls into a small container including the substrate for the horseradish peroxidase or alkaline phosphatase, causing a color to develop. In the case of a fluorophore label, the eluted product falls directly into the detection chamber of a fluorometer for readout. The reagents are introduced to the filter disk either by a syringe, or by continuous pumping through tubing. The latter technique allows a continuous, flow-through monitoring of PCR samples as they are produced.

Without further elaboration, it is believed that one skilled in the art, using the preceding description, can utilize the present invention to its fullest extent. The following preferred specific embodiments are, therefore, to be construed as merely illustrative, and not limiting in any way whatsoever, or of the remainder of the disclosure.

The following various experiments demonstrate that a toxin can be detected by identifying in a sample the DNA that encodes the toxin. The particular examples include amplification of the toxin genes for several strains of *Clostridium botulinum.* Samples tested included both crude bacterial lysates, provided by Fort Detrick, Md., as well as purified toxin protein preparations purchased from SIGMA Chemicals. Such purified preparations are also available from Wako Chemicals.

EXAMPLES

Example 1

A crude, unpurified type D *Clostridium botulinum* (BotD) toxin preparation, and a DNA extract of the same crude toxin preparation, were selected as samples. Each was amplified and detected separately. The nucleic acid sequence coding for this toxin is known.

Ten μl of each BotD DNA sample (0.5 mg./0.5 ml 0.2 M NaCl, 0.05 M Na acetate, pH 6.0) was prepared as follows:

0.5 ml toxin preparation was added to an equal volume of saturated phenol. The resultant mixture was vortexed briefly, and centrifuged for 5 min. at 14,000×g. The supernatant was recovered and the phenol extraction step was repeated on the recovered supernatant. An equal volume of chloroform was added to the supernatant recovered from the repeated phenol extraction. The supernatant was removed and chloroform extraction repeated. The DNA was then precipitated as a pellet from supernatant ethanol. The pellet was then resuspended in 50 μl distilled $H_2O$.

The preparation was added to the conventional PCR reagents Taq polymerase, a buffer, and a mixture of deoxyribonucleotide triphosphates. The following pair of oligonucleotide primers was also added to the solution:

BotD1 5'-TGA CAT GGC CAG TAA AAG-3' (SEQ ID NO: 1)

BotD2 5'-TGT TCC AAA CCC TTC AAA-3' (SEQ ID NO: 2)

These primers were designed by co-inventor James Campbell, of the Naval Research Laboratory, and synthesized by the Synthecell Corporation of Gaithersburg, Md. These primers are specific oligonucleotide pairs designed to match unique DNA sequences in the gene encoding type D botulin toxin.

The thus prepared reaction mixture was used in PCR by thermally cycling for two minutes at three successive temperatures.

1. A high "denaturing" temperature (94° C.);
2. A low "annealing" temperature (52° C.);
3. An intermediate "extension" temperature (about 72° C.).

This thermal cycle was repeated 30 times so that the target DNA was amplified sufficiently to permit its detection, resulting in an approximately one million-fold amplification of the target DNA.

The PCR product was examined by electrophoresing a small portion thereof through an agarose gel, staining with ethidium bromide, and viewing the stained gel under U.V. light. Since it is known in advance what size piece of the toxin gene was bracketed by the two primers, a positive result was indicated for each sample by the appearance of a single stained band of DNA of the appropriate size, at the predicted M.W. (500 bp).

Example 2

A crude, unpurified type A *Clostridium botulinum* (BotA) toxin preparation, and a DNA extract of the same crude toxin preparation, were selected as samples. Each sample was amplified and analyzed separately. The nucleic acid sequence coding for this toxin is known.

Ten μl of the preparation made according to the steps set out in Experiment 1 was added to an aqueous solution including the same conventional PCR reagents as in Example 1, except that the primer pair consisted of BotA1 and BotA3. These primers were designed by co-inventor James Campbell to match unique DNA sequences in the gene encoding type A botulism toxins, and synthesized by the Synthecell Corporation. Primer sequences are as follows:

Bot A1 5'-ATT AAT TAT AAA GAT CCT-3' (SEQ ID NO: 3)

Bot A3 5'-AAC TTC AAG TGA CTC CTC-3' (SEQ ID NO: 4)

The thus prepared reaction mixture was cycled thermally for two minutes at three successive temperatures.

1. A high "denaturing" temperature (94° C.);
2. A low "annealing" temperature (52° C.); and
3. An intermediate "extension" temperature (72° C.).

This thermal cycle was repeated 30 times.

The PCR product was examined by electrophoresing a small portion thereof through an agarose gel, staining with ethidium bromide, and viewing the stained gel under U.V. light. Since it is known in advance what size piece of the toxin gene was bracketed by the two primers, a positive result was indicated for each sample by the appearance of a single stained band of DNA which is of the appropriate size at the predicted M.W. (585 bp).

The same method has been used to detect the botulinum toxin produced by the remaining *Clostrium botulinum* strains B, C, E and F, as well as other toxins by using appropriate PCR primers.

The preceding examples can be repeated with similar success by substituting the generically or specifically described reactants and/or operating conditions of this invention for those used in the preceding examples.

The present invention's use of genetic material to identify a protein toxin provides an alternative (second) technology for verification of the above-described conventional methods that depend on antibody or protein analysis.

As described above, the present invention relies on the principle that PCR provides an efficient and quick mechanism to amplify contaminating nucleic acid sequences. While the actual concentration of the relevant nucleic acid sequence in the sample may be as low as 1/1000 of the toxin concentration, increasing the concentration of the sequence a million-fold prior to analysis greatly facilitates detection of the sequence. Methods which can screen for the characteristic sequence after amplification are then more successful in indicating the presence of biological toxins than testing directly for the biological toxin itself.

The ultimate detection sensitivity level of the present invention is not yet known. However, the minute amount of toxin gene DNA found as a contaminant in as little as 100 picograms of protein could be specifically detected.

The selection of target nucleic acid for amplification, rather than the detection of the microorganism making a toxin may permit the present invention to detect toxins that have been genetically engineered. For example, the present invention detects the presence of the botulin gene in any organism, thus indicating that the organism is potentially capable of producing the botulin toxin, regardless of whether the gene for that toxin was naturally present in the organism or whether the gene was inserted into the organism by genetic manipulation.

As shown above, the present invention is even effective if the toxin has become denatured. That is, the residual DNA is still present and can be amplified, regardless of the condition of the toxin. This provides distinct benefits over conventional methods. That is, the present invention makes testing far more reliable than with the conventional methods testing for the toxins per se, which fail if the toxin is denatured. Further, with the conventional tests, special precautions must be taken to protect laboratory workers and prevent escape of the toxin into the environment. The precautions usually require specially equipped, expensive laboratories and sometimes government clearance. With the present invention, the toxin can be rendered harmless before testing, but its presence can still be detected based on the residual DNA. As a result, testing can be performed less expensively, in more laboratories, and more safely.

Further, the present invention basically requires only a commercially available thermal cycler, PCR reagents and a readout device to perform the amplification and detection. As such, a small transportable system can be used in the field to carry out the present invention. The system is not envisioned as something to be carried around by soldiers in combat to detect biological warfare agents. However, the system could be located in a region of conflict. Other practical uses of the system include: detection of the presence of toxin contamination of a water supply; testing commercial toxin preparations for the presence of DNA, even though these preparations are supposedly purified; detection of the presence of toxins in food or beverages; and detection of the presence of biological toxins at sites which are under review by an international investigative or oversight body.

The foregoing is considered illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to that fall within the scope of the invention and the appended claims.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
(A) LENGTH: 18 base pairs
(B) TYPE: nucleic acid
(C) STRANDEDNESS: single stranded
(D) TOPOLOGY: circular (ii) MOLECULE TYPE: Other nucleic acid (iii) HYPOTHETICAL: no (iv) ANTI-SENSE: no (xi) SEQUENCE DESCRIPTION: SEQ ID NO: 1:

TGACATGGCC AGTAAAAG 18

(2) INFORMATION FOR SEQ ID NO:2:

(i) SEQUENCE CHARACTERISTICS:
(A) LENGTH: 18 base pairs
(B) TYPE: nucleic acid
(C) STRANDEDNESS: single stranded
(D) TOPOLOGY: circular (ii) MOLECULE TYPE: Other nucleic acid (iii) HYPOTHETICAL: no (iv) ANTI-SENSE: no (xi) SEQUENCE DESCRIPTION: SEQ ID NO:2:

TGTTCCAAAC CCTTCAAA 18

(2) INFORMATION FOR SEQ ID NO:3:

(i) SEQUENCE CHARACTERISTICS:
(A) LENGTH: 18 base pairs
(B) TYPE: nucleic acid
(C) STRANDEDNESS: single stranded
(D) TOPOLOGY: circular -continued

```
    (ii) MOLECULE TYPE:   Other nucleic acid

   (iii) HYPOTHETICAL:  no

    (iv) ANTI-SENSE:  no

    (xi) SEQUENCE DESCRIPTION:  SEQ ID NO:3:

ATTAATTATA AAGATCCT                                                    18


(2) INFORMATION FOR SEQ ID NO:4:

     (i) SEQUENCE CHARACTERISTICS:
          (A) LENGTH:  18 base pairs
          (B) TYPE:  nucleic acid
          (C) STRANDEDNESS:  single stranded
          (D) TOPOLOGY:  circular

    (ii) MOLECULE TYPE:   Other nucleic acid

   (iii) HYPOTHETICAL:  no

    (iv) ANTI-SENSE:  no

    (xi) SEQUENCE DESCRIPTION:  SEQ ID NO:4:

AACTTCAAGT GACTCCTC                                                    18
```

What is claimed is:

1. A method for detecting a DNA coding for a toxin of biological origin or a DNA coding for an enzyme specific to toxin production, said toxin suspected of being present in a sample known not to contain any organisms which produce said toxin, comprising the steps of:

a) performing an amplification on said sample which is suspected of containing a unique DNA having a unique sequence of nucleotides coding for the toxin or for an enzyme specific to toxin production, said sample not containing any organisms which produce said toxin, by initiating a polymerase chain reaction with a pair of primers complementary to said ends of said sequence of nucleotides and a polymerase which catalyzes said polymerase chain reaction, said amplification being sufficiently great that the amount of DNA other than said unique DNA in the amplified sample is negligible in comparison to the amount of said unique DNA in the amplified sample if said unique DNA is present in the unamplified sample; and b) detecting the presence of amplified unique DNA in said amplified sample.

2. The method as recited in claim 1, wherein the toxin is selected from the group consisting of botulin, tetanus, ricin, cholera, diphtheria, aflatoxins, perfringens toxin, mycotoxins, shigatoxin, staphylococcal enterotoxin B, T2, seguitoxin, saxitoxin, abrin, cyanoginosin, alphatoxin, tetrodotoxin, aconotoxin, snake venom and spider venom.

3. The method as recited in claim 1, further comprising the step of:

performing a further amplification on said amplified sample by initiating a polymerase chain reaction with a pair of primers complementary to a unique sequence of nucleotides within said amplified unique sequence of nucleotides and a polymerase which catalyzes said polymerase chain reaction, at least one member of said second pair of primers having a detection label bound thereto, thereby producing a detectable amount of double stranded, twice-amplified DNA with said detection label on at least one end thereof if said toxin is present in the unamplified sample.

4. The method as recited in claim 3, wherein said detection of the presence of amplified unique DNA in said amplified sample in step (b) comprises the steps of:

(1) spotting said twice-amplified sample directly on a membrane, and (2) detecting any labelled DNA using one of spectroscopic, photochemical, biochemical or immunochemical techniques.

5. The method as recited in claim 1, wherein said detection of the presence of amplified unique DNA in said amplified sample in step (b) comprises the steps of:

(1) using gel electrophoresis to separate any DNAs in the sample;

(2) denaturing the DNAs;

(3) adsorbing the denatured DNAs on a nitrocellulose membrane;

(4) incubating the nitrocellulose membrane under renaturing conditions with a solution containing fluorescent or radio-labelled molecules able to base pair with said unique DNA; and (5) detecting the position and size of the labelled, unique DNA using autoradiography or fluorometry.

6. The method as recited in claim 1, wherein said detection of the presence of amplified unique DNA in said amplified sample in step (b) comprises the steps of:

placing any amplified DNA in a matrix of agarose through which said amplified DNA moves under the influence of an electric or magnetic field; and identifying said unique DNA based on its mobility in said matrix.

7. The method as described in claim 3, wherein at least one of said primers used in said further amplification includes a specific binding site for a double-stranded DNA binding protein, and wherein any of said twice-amplified DNA present includes said specific binding site at one end and a biotin molecule at its other end.

8. The method as recited in claim 7, wherein said detection of the presence of amplified unique DNA in said amplified sample in step (b) comprises the step of:

(1) using a capture reagent on a membrane attached to an absorptive pad;

(2) reacting any of said twice-amplified DNA, including said double stranded DNA binding site and said biotin molecule, with a color reagent to form a complex;

(3) applying the complex to a membrane attached to an absorptive pad, said membrane having bound thereto a double-stranded DNA-binding protein, whereupon the mixture is captured on the membrane;

(4) detecting the color on the membrane.

9. The method as recited in claim 7, wherein said detection of the presence of amplified unique DNA in said sample in step (b) comprises the steps of:

(1) using gel electrophoresis to separate any DNAs in the sample;

(2) denaturing the DNAs;

(3) adsorbing the denatured DNAs on a nitrocellulose membrane;

(4) incubating the nitrocellulose membrane under renaturing conditions with a solution containing fluorescent or radio-labelled molecules able to base pair with said unique DNA; and (5) detecting the position and size of the labelled, unique DNA using autoradiography or fluorometry.

10. The method as recited in claim 3, wherein the detection label is selected from the group consisting of biotin, fluorophores and chromophores.

11. A method for detecting a plurality of DNAs coding for toxins of biological origin or DNAs coding for enzymes specific to production of said toxins in a sample suspected of including at least one of said toxins and known not to contain any organisms which produce said at least one toxin, comprising the steps of:

a) performing an amplification on said sample which is suspected of containing a plurality of unique DNAs each having a unique sequence of nucleotides coding for a respective one of said toxins or for an enzyme specific to production of a respective one of said toxins, said sample not containing any organisms which produce said toxin, by initiating a polymerase chain reaction with a plurality of pairs of primers, each pair of said plurality of primers being complementary to said ends of a respective one of said sequences of nucleotides, and a polymerase which catalyzes said polymerase chain reaction, said amplification being sufficiently great that the amount of DNA other than said unique DNAs in the amplified sample is negligible in comparison to the amount of said unique DNA in the amplified sample if any of said unique DNAs is present in the unamplified sample; and b) detecting the presence of any of said amplified unique DNAs in said amplified sample.

12. The method as recited in claim 11, further comprising the step of:

performing a further amplification on said amplified sample by initiating a polymerase chain reaction with a plurality of pair of primers, each pair of primers being complementary to a unique sequence of nucleotides within a respective one of said unique sequences of nucleotides and a polymerase which catalyzes said polymerase chain reaction, at least one member of each of said second pairs of primers having a detection label bound thereto, thereby producing a detectable amount of double stranded, labelled, twice-amplified DNA if any one of said toxins is present in the unamplified sample.

13. The method as recited in claim 12, wherein the label associated with each primer pair is unique to said primer pair, thus permitting specific identification of the particular nucleotide sequence amplified.

14. The method as recited in claim 12, wherein said detection of the presence of amplified unique DNA in said amplified sample in step (b) comprises the steps of:

(1) spotting said twice-amplified sample directly on a membrane, and (2) detecting any of said labelled DNAs present on said membrane using one of spectroscopic, photochemical, biochemical or immunochemical means.

15. The method as recited in claim 11, wherein said detection of the presence of amplified unique DNA in said amplified sample in step (b) comprises the steps of:

(1) using gel electrophoresis to separate any DNAs in the sample;

(2) denaturing the DNAs;

(3) adsorbing the denatured DNAs on a nitrocellulose membrane;

(4) incubating the nitrocellulose membrane under renaturing conditions with a solution containing fluorescent or radio-labelled molecules able to base pair with said unique DNAs; and (5) detecting the position and size of any of said labelled, unique DNAs present on said membrane using autoradiography or fluorometry.

16. The method as recited in claim 11, wherein said detection of the presence of amplified unique DNA in said amplified sample in step (b) comprises the steps of;

placing any amplified DNA in a matrix of agarose through which said amplified DNA moves under the influence of an electric or magnetic field; and identifying said unique DNA based on its mobility in said matrix.

17. The method as described in claim 12, wherein at least one member of each of said primer pairs used in said further amplification includes a specific binding site for a double-stranded DNA binding protein, and wherein all of said twice-amplified DNAs present include said specific binding site at one end and a biotin molecule or a fluorophore at its other end.

18. The method as recited in claim 17, wherein said detection of the presence of amplified unique DNA in said amplified sample in step (b) comprises the step of:

(1) using a capture reagent on a membrane attached to an absorptive pad;

(2) reacting any of said twice-amplified DNAs present, including said double stranded DNA binding sites and said biotin molecules, with a color reagent to form a complex;

(3) applying the complex to a membrane attached to an absorptive pad, said membrane having bound thereto a double-stranded DNA-binding protein, whereupon the complex is captured on the membrane; and (4) detecting the color on the membrane.

19. The method as recited in claim 17, wherein said detection of the presence of amplified unique DNA in said amplified sample in step (b) comprises the steps of:

(1) binding a double-stranded DNA-binding protein to a solid support;

(2) occupying all double-stranded DNA-binding sites of said protein on said solid support by treating said support with a color indicator which occupies said binding sites of said protein but has a significantly lower affinity for said binding sites of said protein than do any of said twice-amplified DNAs present in the sample;

(3) treating the solid support with the twice-amplified sample amplified sequences having a normal affinity for said binding sites whereupon any of the twice-amplified DNAs present in said twice-amplified sample displaces said indicator from said support; and (4) colorimetrically or fluorometrically detecting the amount of said indicator displaced from said support.

20. The method as recited in claim 1, wherein said sample is an environmental sample, water supply sample, purified commercial toxin preparation, food or beverage sample, blood sample, mucous sample, saliva sample and urine sample.

21. The method as recited in claim 20, wherein said environmental sample is an air, soil, surface swipe, or water sample.

22. The method as recited in claim 11, wherein said sample is an environmental sample, water supply sample, purified commercial toxin preparation, food or beverage sample, blood sample, mucous sample, saliva sample and urine sample.

23. The method as recited in claim 22, wherein said environmental sample is an air, soil, surface swipe, or water sample.

24. The method as recited in claim 1, wherein said method consists essentially of steps (a) and (b).

25. The method as recited in claim 11, said method consists essentially of steps (a) and (b).

* * * * *